United States Patent [19]
Bosin et al.

[11] Patent Number: 4,971,974
[45] Date of Patent: Nov. 20, 1990

[54] BENZOTHIOPHENES AS APPETITE SUPPRESSANTS

[75] Inventors: Talmage Bosin, Bloomington, Ind.; Robert S. Bitner, Mountain View; Theresa M. Gadbois, Menlo Park; Victor C. Yu, Fremont; Stephen S. Bowersox, Menlo Park, all of Calif.

[73] Assignee: Neurex Corporation, Menlo Park, Calif.

[21] Appl. No.: 207,652

[22] Filed: Jun. 16, 1988

[51] Int. Cl.$^5$ ............................................. A61K 31/44
[52] U.S. Cl. .................................................... 514/291
[58] Field of Search ........................ 514/277, 909, 290

[56] References Cited

U.S. PATENT DOCUMENTS

| | | | |
|---|---|---|---|
| 3,516,278 | 6/1970 | Suh | 260/294.8 |
| 3,636,218 | 1/1972 | Suh | 424/263 |
| 3,704,237 | 11/1972 | Suh | 260/294.8 |
| 3,752,820 | 8/1973 | Suh | 260/294.8 |
| 4,309,445 | 1/1982 | Wurtman et al. | 424/325 |
| 4,745,122 | 5/1988 | Lassen | 514/909 |

OTHER PUBLICATIONS

W. Herz, *J Am Chem Soc*, 72:4999 (1950).
E. Campaigne et al, *J Heterocyclic Chem*, 2:231–235 (1965).
E. Campaigne et al, *J Heterocyclic Chem*, 3:46–50 (1966).
E. Campaigne et al., *J Med Chem* 11:1049–1054 (1968).
F. P. Miller et al, *The Pharmacologist* (1971) 13:207 (#089).
T. Bosin et al, *Adv in Drug Res* (1977), 11:191–233.
E. Campaigne et al, *J Heterocyc Chem* (1979), 16:1321–1324.
A. H. Glassman et al., *Science* (1984), 226:864–866.
P. H. Anderson et al., *Eur J Pharmacol* (1987), 137:291–292.

*Primary Examiner*—Douglas W. Robinson
*Assistant Examiner*—Kevin E. Weddington
*Attorney, Agent, or Firm*—Peter J. Dehlinger

[57] ABSTRACT

Compositions comprising a compound of formula 1, and optionally a mild stimulant, are effective anorectics, where formula 1 is:

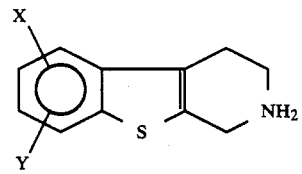

and its pharmaceutically acceptable acid-addition salts, wherein X and Y are each independently hydrogen, hydroxy, methyl, ethyl, propyl, methoxy, ethoxy, propoxy, fluoro, chloro, or bromo.

These compounds are effective for reducing appetite globally, or at lower dosage, for altering macronutrient preferences and decreasing substance dependence.

1 Claim, 10 Drawing Sheets

BENZOTHIOPHENES AS APPETITE SUPPRESSANTS

FIELD OF THE INVENTION

This invention relates to compositions and methods for suppressing appetite, modifying macronutrient preferences, and effecting weight loss in a subject animal.

BACKGROUND OF THE INVENTION

Compounds containing the benzothiophene nucleus exhibit a broad range of pharmacological activities. Triaryl ethylene derivatives exhibiting estrogenic and/or estrogen antagonist properties have shown anti-fertility properties in rodents, as have several 4-aminobenzo[b]thiophenes, tetrahydrodibenzothiophene carboxylic acids, and 4-keto-4,5,6,7-tetrahydrobenzo[b]thiophenes. A number of phenyl- and thienyl-substituted benzo[b]thiophene acetic acids, 2-arylbenzo[b]thiophen-3(2H)-one 1,1-dioxides, benzo[b][2,3-d]pyrimidines, and benzo[b]thiophene 2- and 3-acetic acid derivatives exhibit anti inflammatory activity in rodents.

Useful anti-adrenergic and anti-anginal activities have been attributed to 3-(4-dialkylaminoalkoxy-3,5-disubstituted)benzoylbenzo[b]thiophenes and antihypertensive and/or diuretic properties to certain 2-imidazolinylaminobenzo[b]thiophenes, cyclopenta[b]-benzo[b]thiophen-3-ones and sulfonamide derivatives of 2,3-dihydrobenzo[b]-thiophene 1,1dioxides. Sulfur analogs of several thiosemicarbazone derivatives, including a series of benzo[b]-thiophene-2- and 3-carboxaldehyde thiosemicarbazones exhibit significant anti-fungal and anti-viral activities; benzo[b]thiophene analogs of 3-methoxymethyl-7-acylaminocephalosporins reportedly possess antibacterial actions.

Centrally active benzo[b]thiophene derivatives include isosteres of psilocin and 5-hydroxytryptamine (serotonin). Several 1H-[1]benzo[b]thieno[2,3-c]pyran derivatives exhibit antidepressant activity, as do amides of benzo[b]thiophene-2carboxylic acids such as 3-bromo-2-(N-morpholinoethyl)benzo[b]thiophene carboximide, which additionally possesses anticonvulsant properties. Central nervous system depressant activity has been claimed for a number of N-[(4-phenyl-1-piperazinyl)alkyl]benzo[b]thiophene-2-carboxyamide and 3-substituted-2,3-dihydro-1H-cyclopenta[b]benzo[b]thiophenes; amides of 2-(3-benzo[b]thienyl)ethylamine and a series of 4-benzo[b]thienyloxyalkyl amidoximes reportedly reduce aggressive behavior in rodents (T. Bosin and E. Campaigne, *Adv in Drug Res* (1977), 11:191-233).

The compounds of the present invention are 1,2,3,4-tetrahydrobenzo[b]thienopyridines, sulfur-containing analogs of tetrahydronorharman, a naturally-occurring plant and animal alkaloid. Little is known about the biological activities of these benzothiophene derivatives apart from the fact that they reportedly inhibit antisocial behavior, cause central nervous system depression, and reduce spontaneous motor activity in several mammalian species (U.S. Pat. No. 3,636,218; U.S. Pat. No. 3,518,278; Miller et al, *The Pharmacologist* (1971) 3:207).

Central monoamine neurotransmitter systems have long been implicated in the regulation of ingestive behavior. Virtually all anorectic agents in current clinical use act upon catecholamine and/or serotonergic mechanisms. Those acting principally upon catecholamine systems possess significant stimulant properties; those acting on serotonergic systems do not. Although stimulant agents reduce food consumption and can lead to significant short-term weight loss, their ethical forms are more frequently abused and produce a higher incidence of adverse side effects than their non-stimulant counterparts.

1,2,3,4-tetrahydrobenzo[b]thieno[2,3-c]pyridine and several substituted derivatives have been disclosed in U.S. Pat. Nos. 3,636,218 and 3,518,278 and claimed as CNS depressants and tranquilizing agents. However, there is no disclosure of anorectic activity.

Disclosure of the Invention 1,2,3,4-tetrahydrobenzo[b]thienopyridines are unique in that they exhibit pharmacological properties consistent with those of both stimulant and non-stimulant anorectics. Besides causing central nervous system depression, we have now found that these compounds are inhibitors of both catecholamine and 5-hydroxytryptamine uptake in crude brain synaptosomal preparations. This may indicate one mechanism of action by which these compounds inhibit food consumption. This theory of mechanism is not intended to limit the scope of Applicants, invention, however. We have discovered these compounds to be anorexigenic, and, at low doses, to selectively suppress carbohydrate cravings without necessarily influencing appetite for other macronutrients.

The present invention provides a pharmacological method for suppressing appetite and altering macronutrient preferences in mammals by administering an effective amount of a 1,2,3,4-tetrahydrobenzo[b]thieno[2,3-c]pyridine compound, preferably additionally coadministering an amount of mild stimulant to counteract CNS depression due to the active compound. Administration of these compounds according to the invention produces dose-related decrements of food intake, and can selectively suppress appetite for specific macronutrients, e.g., carbohydrates. Because of their anorexigenic properties, compounds of the present invention are useful as dieting aids in both medicinal and veterinary practice. Due to their special ability to selectively inhibit carbohydrate intake at low doses, compounds of the present invention are additionally useful for treating individuals with abnormal or excessive appetite for carbohydrate-rich foods. This activity correlates with activity against chemical dependency conditions, such as alcoholism, tobacco addiction, and opiate addiction. The present invention thus further comprises a method for treating substance cravings and bulemic syndromes in which a subject (not necessarily obese) experiences powerful urges to consume carbohydrate-containing foods at specific times of the day or night.

Another aspect of the invention is a composition for effecting appetite reduction in a mammal, which composition comprises:

a pharmaceutically acceptable excipient; and
a compound of formula 1:

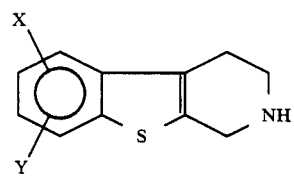

where X and Y are each independently H, hydroxy, methyl, ethyl, propyl, methoxy, ethoxy, propoxy, fluoro, chloro, or bromo. Preferably, compositions of the invention additionally comprise an amount of mild stimulant sufficient to counteract the CNS depressive effects of the compound of formula 1.

Modes of Carrying Out the Invention

A. Definitions

The term "effective amount" refers to that amount of a compound of formula 1 which effects a measurable change in food intake when administered. The precise effective amount required will vary with the particular compounds employed, the species, age and condition subject to be treated. However, the effective amount may be determined by one of ordinary skill in the art with only routine experimentation, following methods known in the art, and disclosed below. In general, an effective amount will range from about 1 to about 100 mg/Kg body weight, preferably about 5–50 mg/Kg, and most preferably about 20 mg/Kg.

The term "appetite-altering amount" refers to the dosage of compound required to alter the appetite for carbohydrates experienced by the subject animal, i.e., to alter the subject's macronutrient preferences. The term "appetite-altering amount" also applies to the quantity required to effect a change in chemical dependency; in other words, a therapeutic amount in the treatment of e.g., alcohol, tobacco, or opiate addiction. The precise appetite-altering amount required will vary with the particular compounds employed, the species, age and condition of the subject to be treated. However, the amount may be determined by one of ordinary skill in the art with only routine experimentation, following methods known in the art, and disclosed below. In general, an appetite-altering amount will be roughly one to two orders of magnitude less than the effective amount described in the preceding paragraph. Thus, the appetite-altering amount will range from about 0.01 to about 10 mg/Kg body weight, preferably about 0.5–5 mg/Kg, and most preferably about 1 mg/Kg.

The term "pharmaceutically acceptable carrier" refers to any generally acceptable excipient that is relatively inert, non-toxic, and non-irritating. As the compositions of the invention are well suited to oral administration, preferred carriers will facilitate formulation in tablet or capsule form. Exemplary carriers include calcium carbonate, sucrose, dextrose, mannose, albumin, starch, cellulose, silica gel, polyethylene glycol (PEG), dried skim milk, rice flour, magnesium stearate, and the like. Carriers for parenteral administration include, without limitation, aqueous solutions of dextrose, saline, pure water, ethanol, glycerol, propylene glycol, peanut oil, sesame oil, polyoxyethylene-polyoxypropylene block polymers, and the like. Suitable formulations and additional carriers are described in Remington's Pharmaceutical Sciences, (17th Ed., Mack Pub. Co., 1985).

The term "mild stimulant" as used herein refers to those pharmaceutical agents useful for counteracting mild CNS (central nervous system) depression, such as caffeine, dyphylline, oxtryphylline, theophylline, deanol acetamidobenzoate, methylphenidate hydrochloride, and the like. Caffeine is presently preferred.

B. General Method

The invention relates to 1,2,3,4-tetrahydrobenzo[b]-thieno[2,3-c]pyridine and substituted derivatives and their use as appetite suppressants. The pharmaceutical compositions of the present invention contain, as active ingredients, one or several compounds of the following formula:

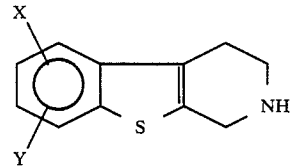

wherein X and Y are each independently hydrogen, hydroxy, halogens such as bromo, chloro, and fluoro, lower alkyl groups of 1 to 3 carbon atoms such as methyl, ethyl, and propyl and lower alkoxy groups such as methoxy, ethoxy, and propoxy. These compounds may be prepared, for example, by the following methods.

Preparation

Basic starting materials used in the preparation of the above-mentioned compounds may include 3-(2-aminoethyl)benzo[b]thiophenes of formula 2:

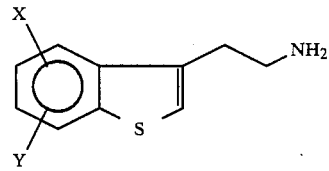

in which X and Y are as previously defined. The ethylamines may be prepared from 3-(2-chloroethyl)benzo[b]-thiophenes and the corresponding cyano compounds by any of several conventional methods described in the literature. (W. Herz, J Am Chem Soc, 72:4999 (1950); Campaigne and Neiss, J Heterocyclic Chem, 2:231 (1965); Campaigne and Neiss, J Heterocyclic Chem, 3:46 (1966); Campaigne et al., J. Med Chem, 16:1321 (1979)). One synthetic process may be illustrated as follows:

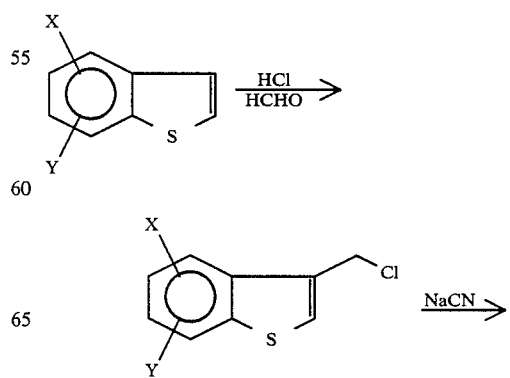

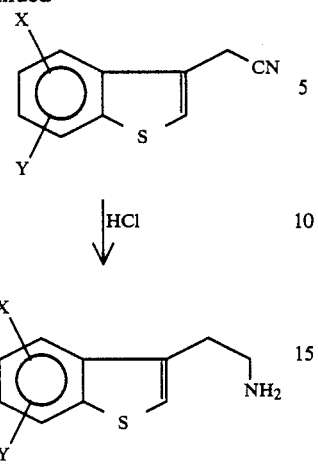

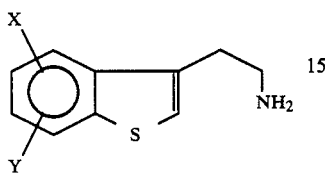

wherein X and Y are as previously described.

Representative of the amines which may be used as starting materials to the compounds of the present invention are the following:

3-(2-aminoethyl)benzo[b]thiophene,
4-bromo-3-(2-aminoethyl)benzo[b]thiophene,
5-bromo-3-(2-aminoethyl)benzo[b]thiophene,
6-bromo-3-(2-aminoethyl)benzo]b]thiophene,
7-bromo-3-(2-aminoethyl)benzo[b]thiophene,
4-chloro-3-(2-aminoethyl)benzo[b]thiophene,
5-chloro-3-(2-aminoethyl)benzo[b]thiophene,
6-chloro-3-(2-aminoethyl)benzo[b]thiophene,
7-chloro-3-(2-aminoethyl)benzo[b]thiophene,
4-fluoro-3-(2-aminoethyl)benzo[b]thiophene,
5-fluoro-3-(2-aminoethyl)benzo[b]thiophene,
6-fluoro-3-(2-aminoethyl)benzo[b]thiophene,
7-fluoro-3-(2-aminoethyl)benzo[b]thiophene,
4-hydroxy-3-(2-aminoethyl)benzo[b]thiophene,
5-hydroxy-3-(2-aminoethyl)benzo[b]thiophene,
6-hydroxy-3-(2-aminoethyl)benzo[b]thiophene,
7-hydorxy-3-(2-aminoethyl)benzo[b]thiophene,
4-methoxy-3-(2-aminoethyl)benzo[b]thiophene,
5-methoxy-3-(2-aminoethyl)benzo[b]thiophene,
6-methoxy-3-(2-aminoethyl)benzo[b]thiophene,
7-methoxy-3-(2-aminoethyl)benzo[b]thiophene, and
5,6-dimethoxy-3-(2-aminoethyl)benzo[b]thiophene.

Compounds of the present invention may be prepared from the aforementioned starting materials by several methods described in the literature (Campaigne and Holmfeld, *J Heterocyclic Chem*, 16:1321 (1979); U.S. Pat. No. 3,636,218). One convenient method involves condensation of ethylamine starting materials with formaldehyde to produce the bis compound which can be acid hydrolyzed to the 1,2,3,4-tetrahydrobenzo[b]thieno[2,3-c]pyridine derivative. The process may be illustrated as follows:

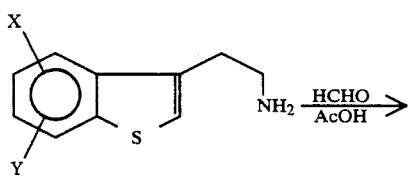

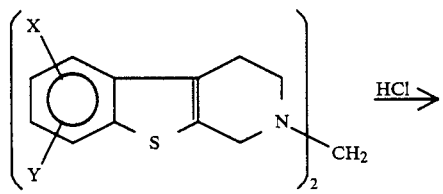

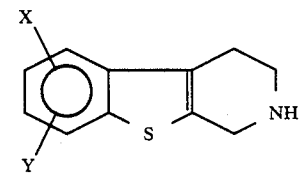

Acid-addition salts of the 1,2,3,4-tetrahydrobenzo[b]thieno[2,3-c]pyridines may be prepared by contacting the free base with a suitable non-toxic acid. Exemplary non-toxic acids include mineral acids such as hydrochloric acid, phosphoric acid, phosphorus acid, and the like, as well as organic acids including, for example, acetic acid, citric acid, maleic acid, tartaric acid, and benzoic acid.

Administration

The present invention comprises, in one aspect, a method of inducing anorexia in animals employing 1,2,3,4-tetrahydrobenzo[b]thieno[2,3-c]pyridine derivatives of formula 1. In another aspect, the present invention comprises a method of altering macronutrient appetite in animals by administering compounds of formula 1. These compounds are administered topically, or by parenteral means, including subcutaneous and intramuscular injection, implantation of sustained-release depots, intravenous injection, intranasal administration, and the like. Such compositions may be aqueous solutions, emulsions, creams, ointments, suspensions, gels, liposomal suspensions, and the like. Thus, suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol ®, vegetable oils, and the like. One may additionally include suitable preservatives, stabilizers, antioxidants, antimicrobials, and buffering agents, for example, BHA, BHT, citric acid, ascorbic acid, tetracycline, and the like. Alternatively, one may incorporate or encapsulate the compound of formula 1 in a suitable polymer matrix or membrane, thus providing a sustained-release delivery device suitable for implantation near the site to be treated locally. Other devices include indwelling catheters and devices such as the Alzet ® minipump. A thorough discussion of pharmaceutically acceptable excipients is available in *Remington's Pharmaceutical Sciences* (Mack Pub. Co.)

In an additional aspect of the present invention, administration of 1,2,3,4-tetrahydrobenzo[b]thieno[2,3-c]pyridines is accompanied by administration of a mild stimulant such as caffeine. The coadministration of the mild stimulant in safe and effective doses is intended to counter CNS depressive effects attributable to 1,2,3,4-tetrahydrobenzo[b]thieno[2,3-c]pyridines. Typical dosage formulations for inducing anorexia would contain from 5–25 mg of the benzo[b]thieno[2,3-c]pyridine as the hydrochloride salt in combination with 25–50 mg caffeine. Typical dosage formulations for altering macronutrient appetite would contain from 0.1–5 mg of the benzo[b] thieno[2,3-c]pyridine as the hydrochloride salt in combination with 5–20 mg caffeine. One or more dosage forms may be administered daily; however, the amount of compound of formula 1 administered will not normally exceed about 100 mg/Kg.

C. EXAMPLES

The following examples are presented to illustrate the present invention, and are not intended to limit the same.

Example 1

Forty-eight 70-to-80-day-old male rats (Bantin & Kingman, Fremont, Calif.) were housed singly in suspended cages, and were acclimated to the laboratory setting for a period of 12 days prior to testing. During this time, they were allowed ad libitum access to food (Ralston-Purina #5001M) and water. The room was kept at 24°–27° C. and maintained on a 12:12-hr light:dark schedule (0700–1900 h).

Animals matched by body weight and mean daily food intake were assigned to 4 groups (n=12/group). Food jars were removed at 0900 h. Twenty-four hours later, rats were injected with either sterile 0.9% saline or saline containing 1,2,3,4-tetrahydrobenzo[b]thieno[2,3-c]pyridine HCl (5, 10, or 25 mg/kg, ip). Preweighed food jars containing meal (Ralston-Purina #5001M) were presented immediately post-injection. These were weighed at intervals over the next 24 hours, and food consumption was calculated for each interval. Animals were provided with water in quantities sufficient for ad libitum consumption throughout the experiment.

Cumulative food intake measures are presented in Table 1. As seen, 1,2,3,4-tetrahydrobenzo[b]thieno[2,3-c]pyridine produces a dose-related decrement in food consumption. At 2 hours post-injection, food intakes for all experimental groups were significantly lower than control values. Rats in the high dose (25 mg/kg) group continued to show substantially lower cumulative food intake at 24 hours post-injection than controls.

TABLE 1

| | Cumulative Food Intake (gm) | | | | |
|---|---|---|---|---|---|
| Dose | 1 hr | 2 hr | 6 hr | 8 hr | 24 hr |
| 0 | 5.3 ± 1.3 | 5.9 ± 1.2 | 8.4 ± 0.9 | 10.4 ± 1.6 | 31.2 ± 2.1 |
| 5 | 1.3 ± 0.6* | 2.5 ± 0.7* | 7.4 ± 1.6 | 9.2 ± 1.6 | 27.4 ± 2.8 |
| 10 | 0.9 ± 0.9* | 2.0 ± 1.1* | 6.3 ± 2.3 | 7.7 ± 2.5 | 26.8 ± 2.8* |
| 25 | 0.1 ± 0.2* | 0.2 ± 0.3* | 2.2 ± 2.4* | 3.0 ± 2.6* | 20.1 ± 2.6* |

Doses in mg/Kg
Data expressed as mean ± SD.
*Significantly different from control (p < 0.02), by two-tailed Student t-test with critical t-values corrected for multiple contrasts.

To assess the duration of the drug-induced anorexia and rebound feeding behavior, food intake was measured at several time intervals after drug administration. Reductions in cumulative food intake shown in Table 1 were attributable to a highly significant fall in food intake occurring in the first hour after drug administration (Table 2). Animals of the 5 and 10 mg/kg groups showed varying degrees of rebound feeding in the 1–6 hr interval after drug injection; however, these were not statistically significant.

TABLE 2

| | Post-Drug Food Intake (gm) | | | | |
|---|---|---|---|---|---|
| Dose | 0–1 hr | 1–2 hr | 2–6 hr | 6–8 hr | 8–24 hr |
| 0 | 5.3 ± 1.3 | 0.6 ± 0.7 | 2.5 ± 1.6 | 2.0 ± 1.0 | 20.8 ± 1.7 |
| 5 | 1.3 ± 0.6* | 1.2 ± 0.6 | 4.9 ± 1.6 | 1.8 ± 1.3 | 18.2 ± 1.9 |
| 10 | 0.9 ± 0.9* | 1.1 ± 0.8 | 4.3 ± 1.8 | 1.4 ± 0.6 | 19.2 ± 2.8 |
| 25 | 0.1 ± 0.2* | 0.1 ± 0.2 | 2.1 ± 2.3 | 0.9 ± 0.7 | 17.1 ± 2.1* |

Doses in mg/Kg
Data expressed as mean ± SD.
*Significantly different from control (p < 0.05), by two-tailed Student t-test with critical t-values corrected for multiple contrasts.

In summary, compositions containing 5 mg/kg of 1,2,3,4-tetrahydrobenzo[b]thieno[2,3-c]pyridine, which is representative of the class, significantly reduce food consumption in rats when administered intraperitoneally. In acute toxicity studies in mice, 1,2,3,4-tetrahydrobenzo[b]thieno[2,3-c]pyridine yields $LD_{50}$ values in excess of 100 mg/kg when administered intraperitoneally and 100 mg/kg when administered by the oral route.

Example 2

(Alteration of Macronut Preference)

This Example demonstrates alteration of macronutrient preference in rats.

Sixty adult male rats (Sprague-Dawley, 225–300 g) were acclimated to laboratory conditions for a period of 10 days, during which they were allowed unrestricted access to food (Ralston-Purina #5001M) and water. All subjects were housed in individual cages, and the animal facility was maintained on a 12:12 hour light:dark cycle at 24°–27° C.

Animals were assigned to 6 groups (10 per group), then allowed to consume, ad libitum, one of two isonitrogenous test diets containing either 75% or 25% carbohydrate. After 3 days, food jars were removed. After an additional 24 hours, rats were administered either saline or 1,2,3,4-tetrahydrobenzo[b]thieno[2,3-c]pyridine (1.5 or 3.0 mg/Kg body weight), then given immediate access to the test diets. Data listed in Table 3 indicate the cumulative amount in grams (mean±SEM) of each diet consumed by the experimental and control groups during the subsequent 2-hour period.

TABLE 3

| | 75% Carbohydrate | | 25% Carbohydrate | |
|---|---|---|---|---|
| Treatment | 1 hr | 2 hr | 1 hr | 2 hr |
| saline | 6.6 ± 0.5 | 8.4 ± 1.6 | 6.4 ± 0.5 | 7.5 ± 1.7 |

TABLE 3-continued

| Treatment | 75% Carbohydrate | | 25% Carbohydrate | |
|---|---|---|---|---|
| | 1 hr | 2 hr | 1 hr | 2 hr |
| Compound 1 (1.5 mg/Kg) | 4.4 ± 0.2* | 5.8 ± 0.8* | 5.6 ± 0.3 | 7.6 ± 1.0 |
| Compound 1 (3.0 mg/Kg) | 4.5 ± 0.2* | 6.0 ± 1.3* | 5.4 ± 0.3 | 7.0 ± 1.1 |

*indicates significantly different from control, $p < 0.01$ by two-tailed Student's t-test.

The results indicate that animals receiving 1,2,3,4-tetrahydrobenzo[b]thieno[2,3-c]pyridine consumed significantly less of the high carbohydrate diet than did controls, but consumed equivalent quantities of the low carbohydrate diet. Thus, compounds of the invention selectively suppress carbohydrate cravings when administered at doses lower than the dosage effective for global reduction in appetite. This demonstrates the utility of the present invention as a method for reducing substance cravings per se, insofar as food cravings model clinical syndromes in which there is excessive preoccupation with, or urges for, specific habituating substances (Glassman et al., Science (1984) 226:864). Accordingly, this Example may be taken as evidencing efficacy in the treatment of alcohol, tobacco, or drug (particularly opiate) addiction.

Example 3

(Formulations)

(A) A representative capsule formulation is prepared as follows:

| Compound | 50.0 mg |
|---|---|
| starch | 3.0 mg |
| magnesium stearate | 3.0 mg |
| lactose | 110.0 mg |
| polyvinylpyrrolidone | 3.0 mg |

The compound of formula 1, starch, magnesium stearate, lactose, and polyvinylpyrrolidone are granulated in methanol, dried, and loaded into capsules. Alternatively, the mixture may be tableted by standard methods.

(B) An oral suspension is prepared as follows:

| Compound | 60.0 mg |
|---|---|
| fumaric acid | 0.5 g |
| NaCl | 2.0 g |
| methyl paraben | 0.1 g |
| granulated sugar | 25.5 g |
| sorbitol (70% aq) | 12.85 g |
| Veegum K | 1.0 g |
| flavorings | 0.035 mL |
| colorings | 0.5 mg |
| distilled water qs | 100.0 mL | the components are mixed together and stored in a sealed vessel.

(D) A formulation suitable for parenteral administration is prepared as follows:

| Compound | 40.0 mg |
|---|---|
| $KH_2PO_4$ buffer (0.4M) | 2.0 mL |
| KOH (1N) qs | pH 7.0 |
| water qs | 20.0 mL |

The components are mixed together and stored under sterile conditions.

What is claimed:

1. A method for suppressing appetite in a mammal, which method comprises:
   administering to a mammal a therapeutically effective amount of a compound of formula 1;

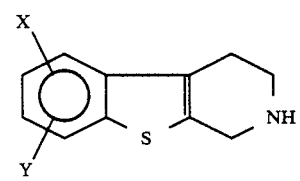

or a pharmaceutically acceptable acid-addition salts, thereof wherein
X and Y are each independently hydrogen, hydroxy, methyl, ethyl, propyl, methoxy, ethoxy, proposy, fluoro, bromo, or chloro.

* * * * *